(12) United States Patent  
Collins et al.

(10) Patent No.: US 8,079,366 B2
(45) Date of Patent: Dec. 20, 2011

(54) MAGNETIC EARPLUG

(76) Inventors: Timothy R. Collins, Chaska, MN (US);
Brian D. Collins, Chaska, MN (US)

( * ) Notice: Subject to any disclaimer, the term of this patent is extended or adjusted under 35 U.S.C. 154(b) by 289 days.

(21) Appl. No.: 12/416,295

(22) Filed: Apr. 1, 2009

(65) Prior Publication Data

US 2009/0250072 A1 Oct. 8, 2009

Related U.S. Application Data

(60) Provisional application No. 61/041,995, filed on Apr. 3, 2008.

(51) Int. Cl.
*A61F 11/00* (2006.01)
*A61B 7/02* (2006.01)
(52) U.S. Cl. ..................... 128/864; 181/135
(58) Field of Classification Search .......... 128/864–868; 181/129–135; 381/328, 396
See application file for complete search history.

(56) References Cited

U.S. PATENT DOCUMENTS

| | | | | |
|---|---|---|---|---|
| 2,246,736 A * | 6/1941 | Knudsen | ................ | 128/867 |
| 3,431,370 A * | 3/1969 | Crosby | ................ | 181/131 |
| 4,936,411 A * | 6/1990 | Leonard | ................ | 181/135 |
| 4,985,925 A * | 1/1991 | Langberg et al. | ................ | 381/71.6 |
| 5,142,587 A * | 8/1992 | Kobayashi | ................ | 381/380 |
| 5,711,313 A | 1/1998 | Fleming | | |
| 5,727,566 A * | 3/1998 | Leight | ................ | 128/857 |
| 5,988,313 A * | 11/1999 | Hakansson | ................ | 181/135 |
| 6,006,857 A * | 12/1999 | Leight et al. | ................ | 181/135 |
| 6,695,093 B1 * | 2/2004 | Falco | ................ | 181/135 |
| 7,712,469 B2 * | 5/2010 | Jenkins, Jr. | ................ | 128/864 |

* cited by examiner

*Primary Examiner* — Patricia Bianco
*Assistant Examiner* — Kari Petrik
(74) *Attorney, Agent, or Firm* — Leanne Taveggia Farrell; Westman, Champlin & Kelly, P.A.

(57) ABSTRACT

An earplug includes a body, a post and a magnet. The body is made of a pliable material and includes a proximal end and a distal end. The proximal end is shaped to be positioned proximal to the user's middle ear and a distal end is shaped to be exposed to the external environment of the user's outer ear when the body is inserted into the user's ear canal. The post is at least partially embedded within the body and includes a first end, a second end and a socket located at one of the first and the second ends. The magnet is positioned in the socket of the post and is capable of producing a permanent magnetic field.

10 Claims, 6 Drawing Sheets

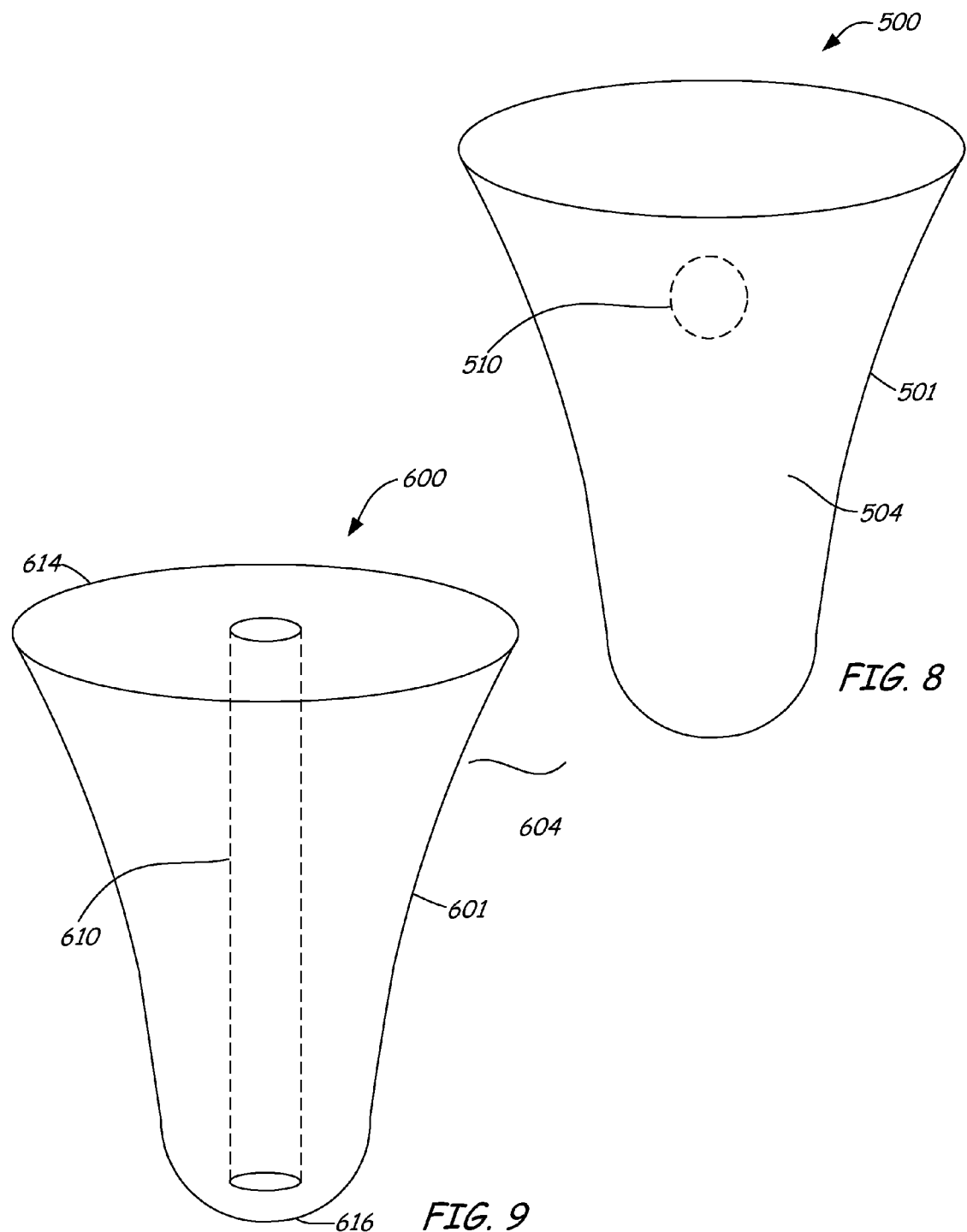

MAGNETIC EARPLUG

BACKGROUND

An earplug is a device that is insertable into the ear canal. Earplugs are widely used in many applications. Example applications include industrial, such as manufacturing; recreation, such as motorcycling, off road sports, trapshooting, range shooting; hunting; construction; agriculture, such as grain handling; mining; military and law enforcement. Earplugs are used to protect the human ear from loud noises generated by machinery, tools, guns, music and etc. common to the listed example applications.

Currently, earplugs are required as part of OSHA's Hearing Conservation Program, which mandates the use of earplugs for any employee whose exposure is equal to or exceeds eight hours of an average of 85 decibels in noise. Without earplugs, any of the applications listed above can produce permanent and irreversible hearing loss and/or damage to one's ears.

Oftentimes, even when earplugs are available, a person fails to use them. The most common explanation is that earplugs were removed, misplaced or lost before or during the activity in question. Earplugs are commonly removed when the user is talking to someone, listening to the surrounding environment, or when the sound level is temporarily lowered. Many devices exist to overcome this "loss" situation. For example, a string or cord connecting the two earplugs can be used to hold the earplugs around the neck when not in use. In another example, a headband clamp can be used that is fastened to the earplugs and stays in place by pinching the head or neck.

The discussion above is merely provided for general background information and is not intended to be used as an aid in determining the scope of the claimed subject matter.

SUMMARY

Embodiments are directed to an earplug including a body, a post and a magnet. The body is made of a pliable material and includes a proximal end and a distal end. The proximal end is shaped to be positioned in proximity to the user's middle ear and a distal end is shaped to be exposed to the external environment of the user's outer ear when the body is inserted into the user's ear canal. In one embodiment, the post is at least partially embedded within the body and includes a first end, a second end and a socket located at one of the first and the second ends. The magnet is positioned in the socket of the post and is capable of producing a permanent magnetic field. In another embodiment, the magnet is embedded in the pliable material of the body. In yet another embodiment, the magnet is coupled to the distal end of the body.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

FIG. 8 illustrates a perspective view of an earplug under yet another embodiment.

FIG. 9 illustrates a perspective view of an earplug under yet another embodiment.

DETAILED DESCRIPTION

Embodiments described pertain to an earplug insertable into a user's ear canal and having a magnet capable of producing a permanent magnetic field. When the earplug is taken out of the ear, the earplug can be easily stored or attached to any ferrous metal object, such as an object made of steel or iron, which is in proximity to the user of the earplug. For example, the magnet located in the earplug can be attached to a firearm if the user is hunting or shooting, to tools or machinery in the user's workspace, to the user's belt buckle, zipper or buttons or to the handle bars or gas tank of motorcycles or other recreational vehicles using the magnet's permanent magnetic field. Since the magnetic earplug is attracted to ferrous metallic objects, the magnetic earplug is thereby securely attached on the ferrous metal object for safekeeping until the magnetic earplug is again needed by the user. In addition, the magnetic coupling of the earplug to another metal object ensures that the earplug will not disconnect even at excessive highway speeds in the example of the use of earplugs with motorcycles or other recreational vehicles. In addition, the magnetic coupling between the earplug and the metal object includes secure coupling even in high vibration environments, such as with use of pneumatic tools, nail guns and other manufacturing machinery.

In another aspect, using an earplug that includes a magnet capable of producing a permanent magnetic field can have therapeutic benefits. Magnetic fields in proximity to the skin of a human body can improve circulation and reduce inflammation by promoting blood flow through the influence of magnetic flux lines interacting with the hemoglobin in the blood. By placing an earplug including a magnet in an ear canal can have at least some therapeutic value.

Figure 1:
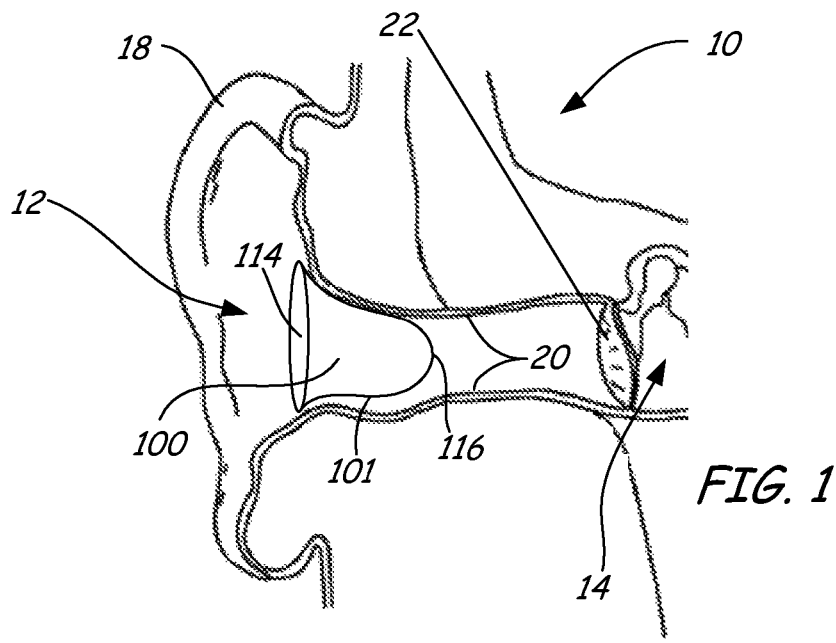
FIG. 1 illustrates a schematic diagram of an earplug as inserted into a user's ear.

FIG. 1 illustrates an ear 10 of a body that enables a person to detect sound. Ear 10 illustrates an outer ear 12 and a middle ear 14. Outer ear 12 collects sound and includes the pinna 18, the ear canal 20 and an outer most layer of the ear drum or tympanic membrane 22. Pinna 18 helps direct sound through ear canal 20 to tympanic membrane 22. Middle ear 14 includes a cavity for transmitting sound. An earplug 100 can be inserted into ear canal 20 to block sound from being collected and transferred. Earplug 100 includes a body 101 made of a pliable material and having a distal end 114 and a proximal end 116. Proximal end 116 is shaped to be inserted into ear canal 20 of a user and positioned in proximity to the user's middle ear 14 and distal end 114 is configured to be exposed to the external environment of the user's outer ear 12.

Figure 2:
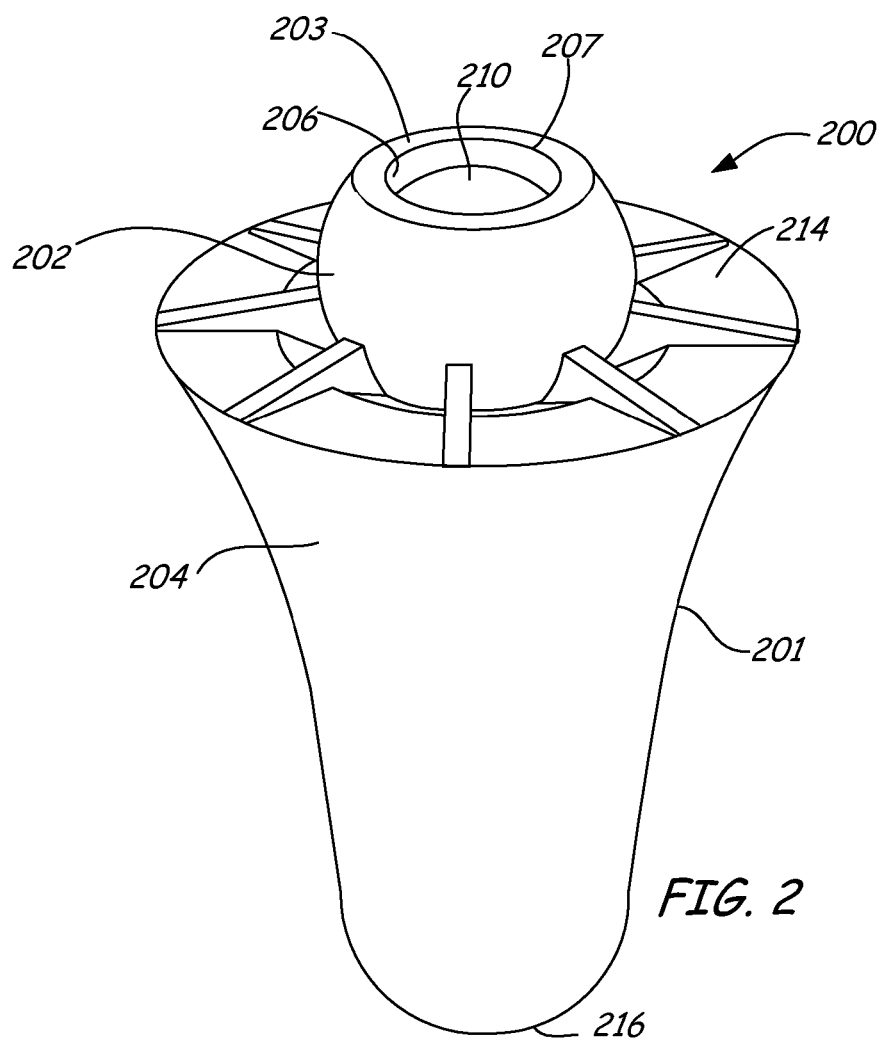
FIG. 2 illustrates another perspective view of an earplug under one embodiment.
Figure 3:
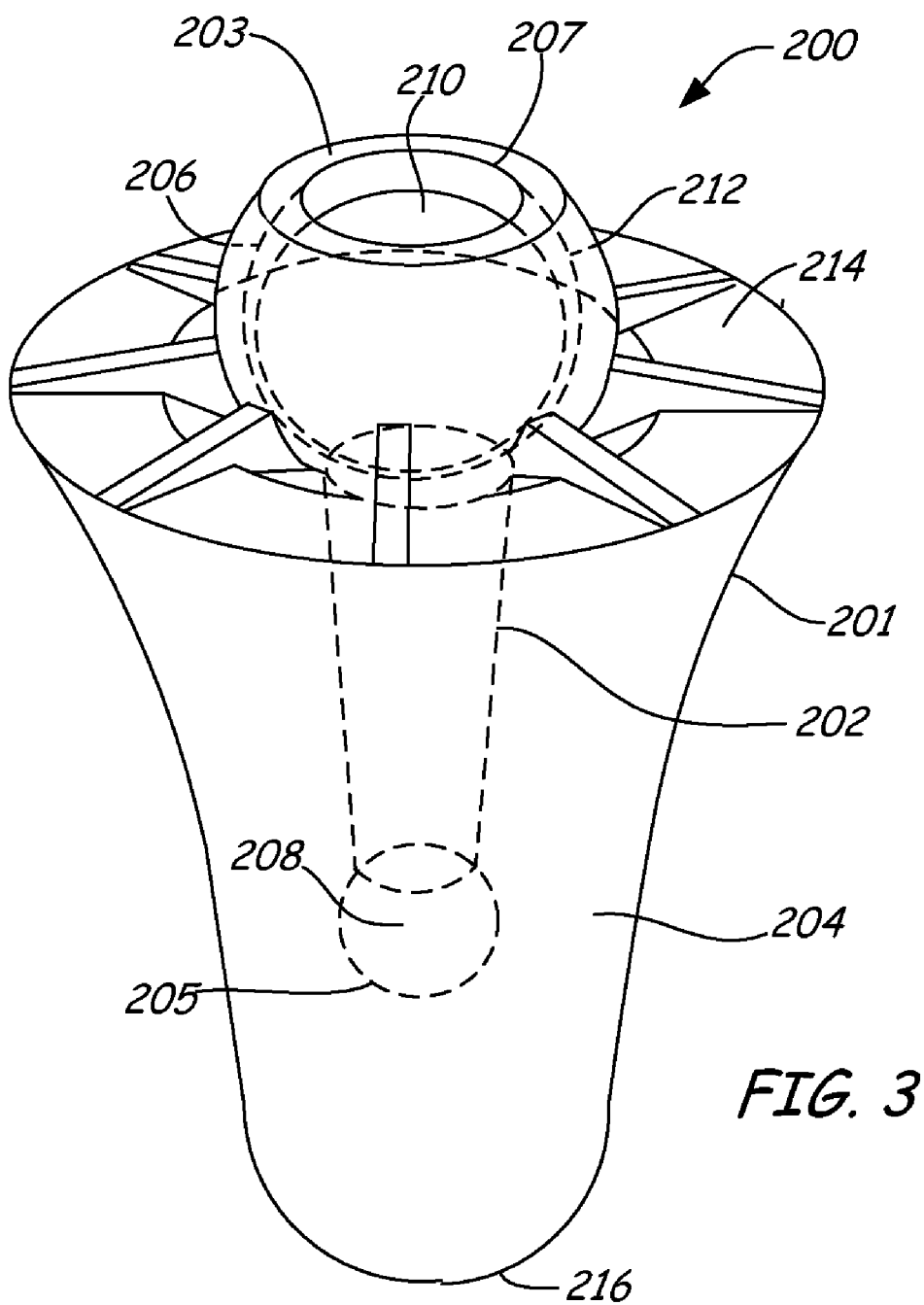
FIG. 3 illustrates a perspective view of the earplug illustrated in FIG. 2.
Figure 4:
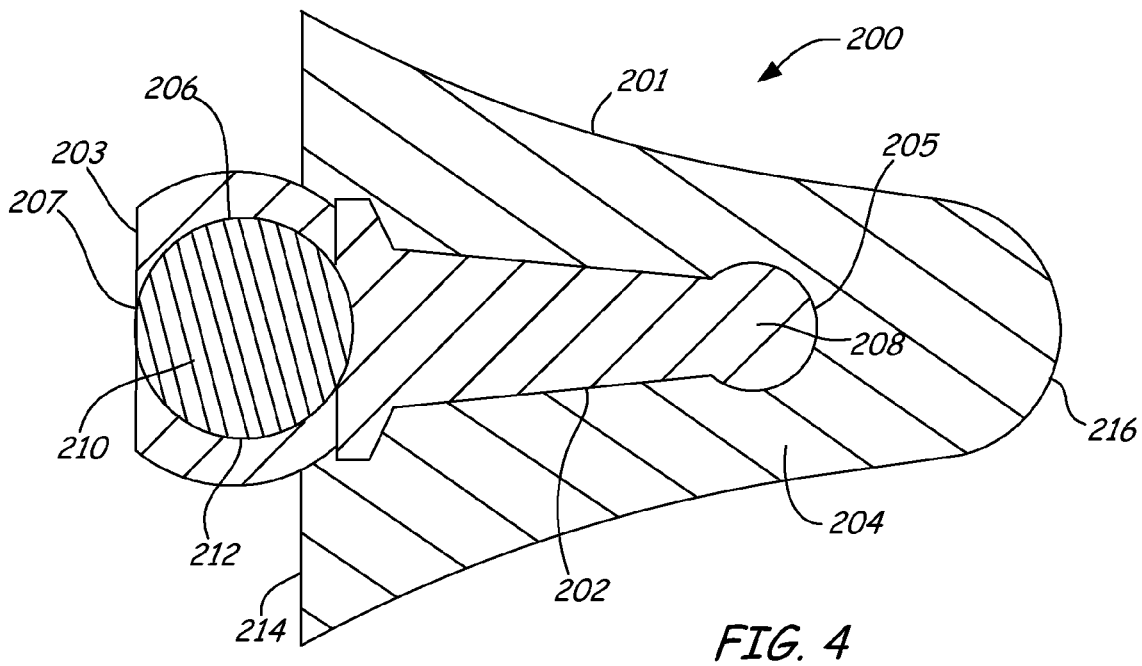
FIG. 4 illustrates a sectional view of the earplug illustrated in FIGS. 2 and 3.
Figure 5:
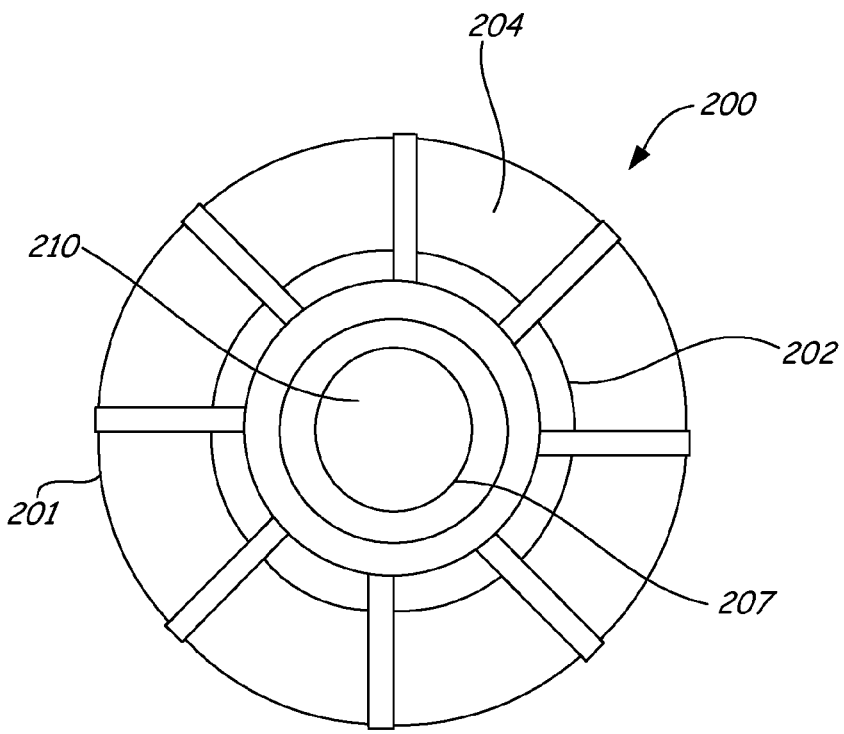
FIG. 5 illustrates a view of a first end of the earplug illustrated in FIGS. 2-4.

FIGS. 2 and 3 illustrate perspective views of an earplug 200 under one embodiment. In FIG. 3, phantom lines are shown to more clearly illustrate the structural components of earplug 200. FIG. 4 illustrates a sectional view of earplug 200 and FIG. 5 illustrates an end view of earplug 200.

Earplug 200 includes a body 201 comprised of a pliable material 204, such as foam. Earplug 200 also includes a post 202. Material 204 of body 201 at least partially surrounds or overmolds at least a portion of post 202. Post 202 includes a first end 203 and a second end 205 (FIGS. 3 and 4). Post 202 includes a socket positioned at first end 203. The socket includes a socket cavity 206 and a socket opening 207.

As illustrated in FIGS. 2-4, a portion of post 202 protrudes from a distal end 214 of body 201. The protruding portion of post 202 includes first end 203 and socket cavity 206, such that socket opening 207 is exposed to the surrounding environment of earplug 200. The portion of post 202 that is surrounded by material 204 includes second end 205 having at least one retention boss 208. As illustrated in FIGS. 3 and 4, retention boss is located at second end 205 of post 202. However, it should be realized that post 202 can include other types of bosses located on other portions of post 202 that are surrounded by material 204. Retention boss 208 provides additional surface area to post 202 for material 204 to overmold to post 202 to provide better material retention. In general, post 202 can be made of a polymer, such as plastic. However, other materials are possible.

Press fitted through socket opening 207 and housed socket in cavity 206 includes a magnet 210. Magnet 210 is capable of producing a permanent magnetic field. For example, magnet 210 can be formed of a ferromagnetic or ferrimagnetic material that can retain its own magnetization and can respond to other magnetic fields. In general, a permanent magnet is made of some type of metallic material that work is applied to in order to magnetize it. One example magnet that can be used includes a neodymium iron boron (NdFeB) material plated with a nickel copper nickel (Ni—Cu—Ni). The magnet can have a magnetic field of approximately 4,850 gauss. The maximum magnetic induction field is 13,200 Gauss, while the maximum magnetic field can be 42 MGOe. It should be noted that other types of magnets or permanents magnets can be used in other embodiments of the earplug.

As illustrated in FIG. 2, magnet 210 has a spherical shape for fitting into spherical socket cavity 206. The spherical shape of magnet 210 allows it to rotate about an inner wall 212 (FIG. 3) of socket cavity 206. A rotatable magnet 210 prevents the magnet from scratching the ferrous object with which magnet 210 is attracted to by allowing the magnet to roll along the object for placement and removal.

Figure 6:
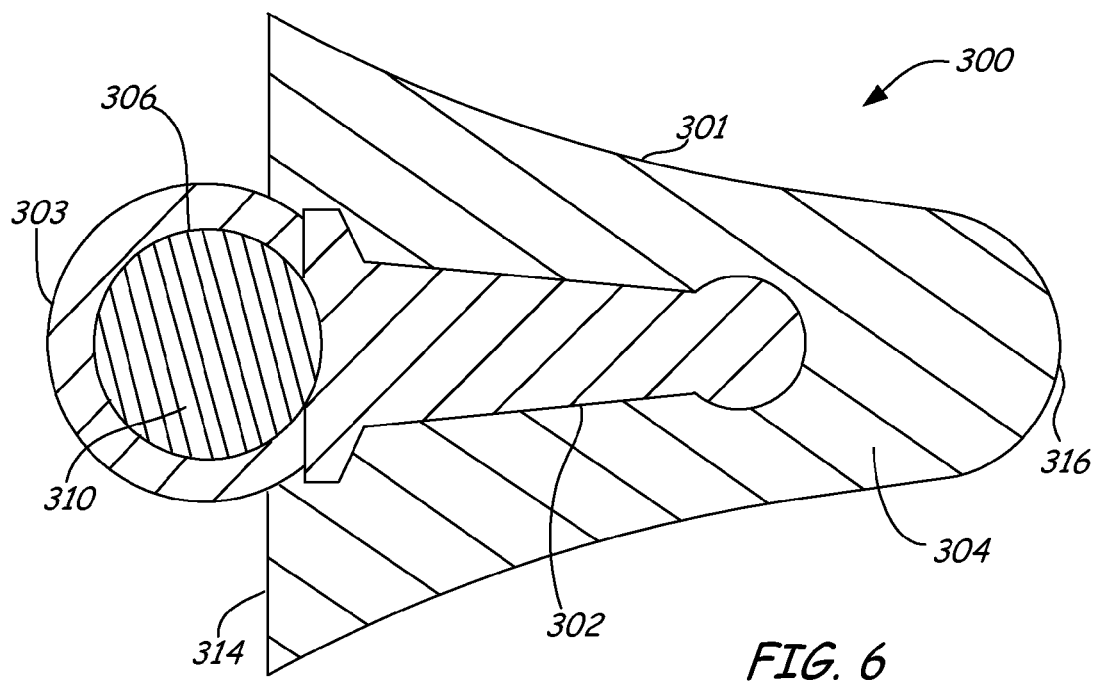
FIG. 6 illustrates a sectional view of an earplug under another embodiment.

FIG. 6 illustrates a sectional view of an earplug 300 under another embodiment. Earplug 300 is like earplug 200 in that it includes a post 302 and a body 301 including a pliable material 304, where the post 302 partially protrudes from a distal end 314 of body 301 and includes a socket 306 at a first end 303 of post 302 for housing a magnet 310 capable of producing a permanent magnetic field. However, instead of magnet 310 being exposed to the environment through an opening in the socket, such as opening 207 in FIG. 2, magnet 310 is enclosed within socket 306 such that it is fully encapsulated by the material of post 302. A fully encapsulated magnet 310 further ensures that magnet 310 will not scratch the surface of a metal object with which it is attracted to.

Embodiments of earplugs 200 and 300 illustrated in FIGS. 2-6 include magnets 210 and 310 that are located at a distal end 214 and 314 versus a proximal end 216 and 316 of bodies 201 and 301. Proximal ends 216 and 316 are shaped for insertion into an ear canal of a user, and distal ends 214 and 314 are the ends that are exposed to the environment of the user's outer ear when the earplugs 200 and 300 are inserted into the ear canal of the user. Protruding magnets 210 and 310 from distal ends 214 and 314 ensure that when the earplug is placed on a metal object, proximal ends 216 and 316 will be the free ends and distal ends 214 and 314 will be constrained to the object. This configuration prevents earplugs 200 and 300 from getting dirty on their proximal end, especially when the earplugs will again be inserted into an ear canal of a user.

Figure 7:
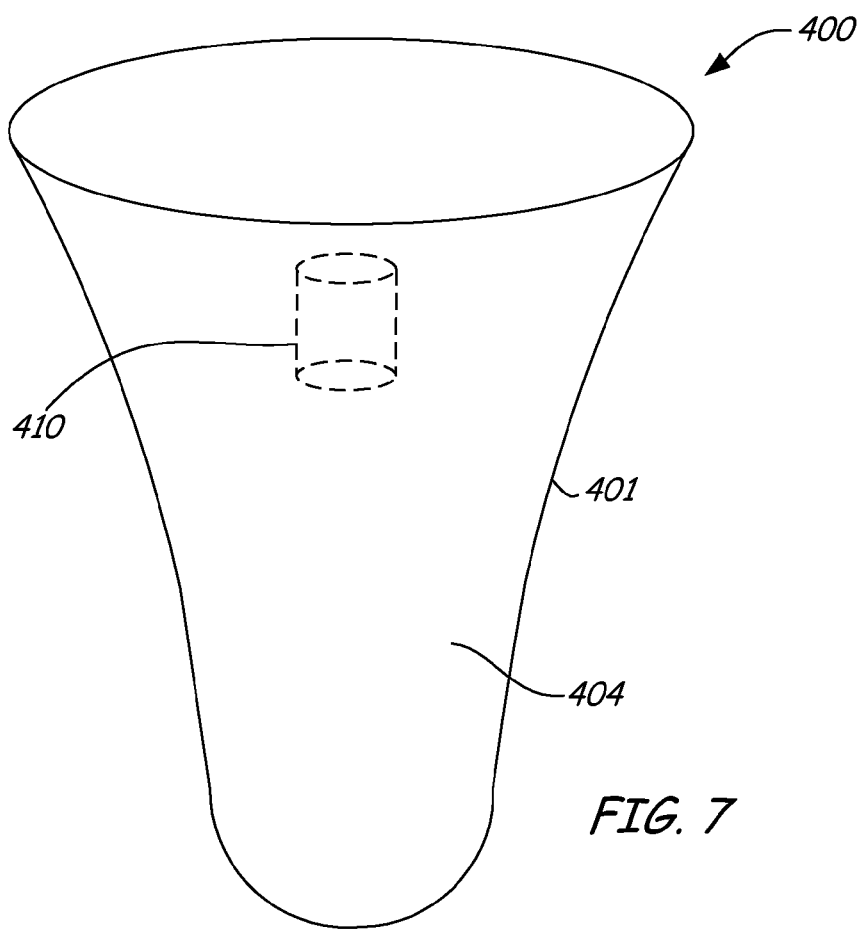
FIG. 7 illustrates a perspective view of an earplug under yet another embodiment.

FIGS. 7-9 illustrate perspective views of earplugs 400, 500 and 600, respectively, in accordance with other embodiments. Earplugs 400, 500 and 600 include magnets 410, 510 and 610 capable of producing a permanent magnetic field that are embedded into bodies 401, 501 and 601 without the use of a post to support the magnet. In FIGS. 7 and 8, magnets 410 and 510 are located and embedded within the pliable material 404, 504 of the body 401, 501 of the earplug in a generally centralized position, while magnet 610 is embedded and extends from distal end 614 into the pliable material 604 of body 601 towards proximal end 616. Although not particularly illustrated in FIGS. 7-9, each of magnets 410, 510 and 610 can include retention bosses for material 404, 504 and 604 to overmold to magnets 410, 510 and 610 to provide better material retention. Although FIGS. 6 and 8 illustrate magnets 410 and 610 as having cylindrical shapes and FIG. 7 illustrating magnet 510 having a spherical shape, magnets 410, 510 and 610 can be any of a variety of three-dimensional shapes.

Figure 10:
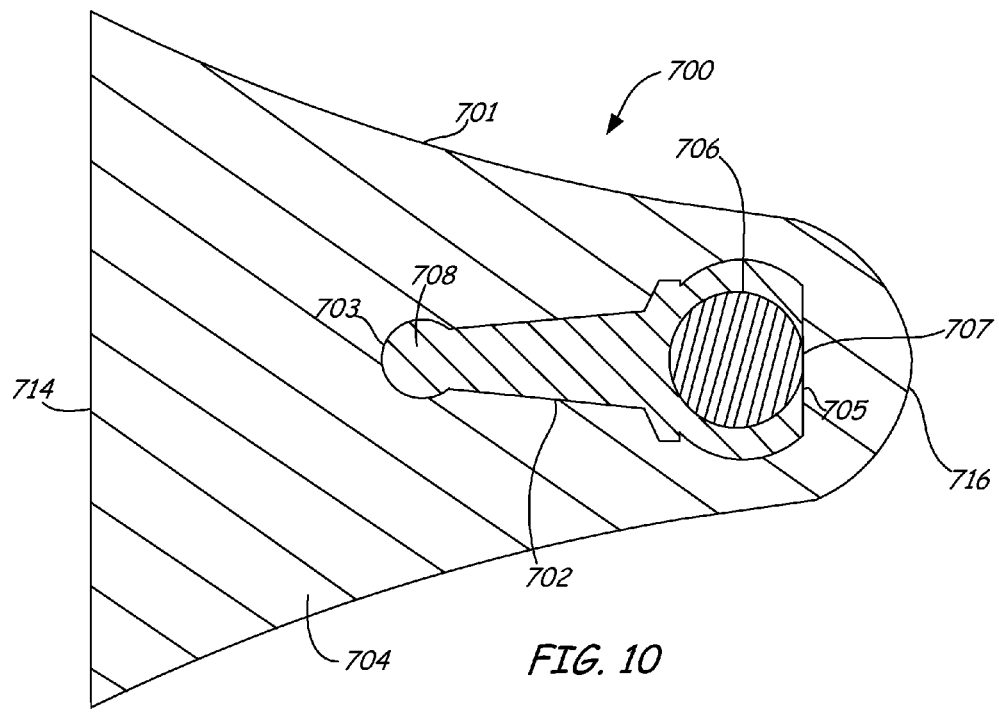
FIG. 10 illustrates a sectional view of an earplug under yet another embodiment.

FIG. 10 illustrates a sectional view of an earplug 700 under yet another embodiment. Like earplug 100, earplug 700 includes a post 702 and a body 701 including a pliable material 704, such as foam. The post 702 is fully embedded in material 704 of body 701 and includes a first end 703 and a second end 705. In FIG. 10, first end 703 of post 702 is in closer proximity to distal end 714 of body 701 and second end 705 is in closer proximity to proximal end 716 of body 701. Unlike FIGS. 2-6, socket 706 is located at second end 705 of post 702 to house a magnet 710 capable of producing a permanent magnetic field.

Socket 706 has a socket opening 707. However, instead of post 702 and magnet 710 protruding from a distal end 714 of the earplug 700 as is the case for earplug 100, post 702 and magnet 710 are fully encapsulated by material 704 and are in closer proximity to proximal end 716. Having magnet 706 in closer proximity to proximal end 716 than distal end 714 allows earplug 600 to attach to a metal object such that the proximal end 716 is magnetically coupled to the metal object and distal end 714 is free. In this configuration, a user can easily grab the earplug without having to rotate the earplug in their hand to stick the proximal end first into the user's ear canal. Like post 102, post 702 can include at least one retention boss 708 to provide better overmold retention of material 704 to post 702. In the embodiment illustrated in FIG. 10, retention boss 708 is located at first end 703 of post 702.

Figure 11:
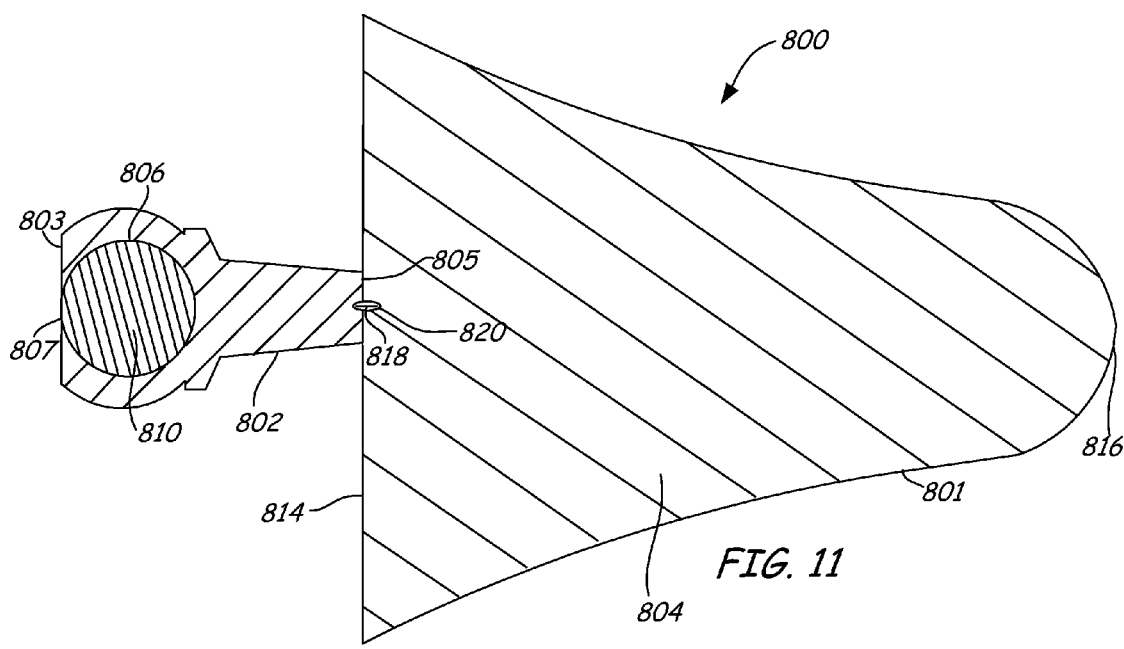
FIG. 11 illustrates a sectional view of an earplug under yet another embodiment.

FIG. 11 illustrates a sectional view of an earplug 800 under yet another embodiment. Like earplug 100, earplug 800 includes a post 802 and a body 801 including a pliable material 804, such as foam. Post 802 has a first end 803 and a second end 805. A magnet 810 capable of producing a permanent magnetic field is housed in a socket or cavity 806 at first end 803. Socket 806 includes a socket opening 807. However, instead of post 802 partially protruding from distal end 814 and partially surrounded by material 804 of body 801, second end 805 of post 802 is coupled to distal end 814 of body 801.

A piece of monofil line 818 is secured into body 801 with adhesive 820 at one end and secured into the material of post 802 with the adhesive at the other end. In particular, monofil line 818 is recessed into body 801 from distal end 814 a distance of ⅜ of an inch and monofil line 818 is recessed into the material of post 802 from second end 805 a distance of 1/16 of an inch.

Like the earplugs illustrated in FIGS. 2-6, when earplug 800 is placed on a metal object proximal ends 816 will be the free end and distal end 814 will be constrained to the object. This configuration can prevent earplug 800 from getting dirty on its proximal end, especially when the earplugs will again be inserted into an ear canal of a user. In addition, post 802 provides a structure for easily pulling earplug 800 out of a user's ear canal.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An earplug comprising:
   a body having a proximal end and a distal end, the body including a pliable material;
   a post at least partially embedded within the pliable material of the body and including a first end, a second end and a socket located at one of the first and the second ends, wherein the socket includes a socket opening and a socket cavity;
   a magnet press fitted through the socket opening and positioned in the socket cavity, the magnet being capable of producing a permanent magnetic field; and
   wherein the magnet is rotatable within the socket cavity.

2. The earplug of claim 1, wherein the socket is located at the first end of the post and protrudes from a distal end of the body and the second end of the post is embedded in the pliable material of the body.

3. The earplug of claim 2, wherein located at the second end opposite the socket comprises a retention boss configured to provide additional surface area to the post for overmold retention of the pliable material to the post.

4. The earplug of claim 2, wherein the socket opening exposes the magnet positioned in the socket cavity to an exterior environment of the earplug.

5. The earplug of claim 1, wherein the socket cavity comprises a spherical socket cavity and the magnet comprises a corresponding spherical shape.

6. The earplug of claim 1, wherein the magnet comprises one of a ferromagnetic and ferrimagnetic material that can retain its own magnetization.

7. An earplug comprising:
   a body having a proximal end shaped to be positioned in proximity to the user's middle ear and a distal end shaped to be exposed to an external environment of the user's outer ear when the body is inserted into the user's ear canal, the body including a pliable material;
   a post including a first section embedded in the pliable material of the body and a second section located external to the pliable material of the body, the second section of the post including a socket having a socket cavity; and
   a permanent magnet positioned within the socket cavity of the post and being capable of rotating within the socket cavity.

8. The earplug of claim 7, wherein the socket further comprises a socket opening.

9. The earplug of claim 8, wherein the first section of the post, which is embedded within the pliable material of the body, includes a retention boss, the retention boss configured to provide additional surface area to the post for overmold retention of the pliable material to the post.

10. The earplug of claim 8, wherein the socket opening exposes the permanent magnet to the external environment of the user's outer ear.

* * * * *